United States Patent
Kiessling et al.

(10) Patent No.: US 10,391,185 B2
(45) Date of Patent: Aug. 27, 2019

(54) MULTIMODAL ULTRASOUND AND PHOTOACOUSTIC CONTRAST AGENT BASED ON POLYMERIC MICROPARTICLES

(71) Applicants: RWTH AACHEN, Aachen (DE); FUJIFILM VisualSonics, Inc., Toronto (CA)

(72) Inventors: Fabian Kiessling, Aachen (DE); Twan Lammers, Maaseik (NL); Stanley Fokong Nyongamsen, Aachen (DE); Katrin Suppelt, Ingolstadt (DE)

(73) Assignees: Fujifilm VisualSonics, Inc., Toronto, Ontario (CA); RWTH Aachen, Aachen (DE)

( * ) Notice: Subject to any disclaimer, the term of this patent is extended or adjusted under 35 U.S.C. 154(b) by 0 days.

(21) Appl. No.: 15/528,946

(22) PCT Filed: Nov. 26, 2015

(86) PCT No.: PCT/EP2015/077827
§ 371 (c)(1),
(2) Date: May 23, 2017

(87) PCT Pub. No.: WO2016/083533
PCT Pub. Date: Jun. 2, 2016

(65) Prior Publication Data
US 2017/0252467 A1 Sep. 7, 2017

(30) Foreign Application Priority Data
Nov. 26, 2014 (EP) .................................... 14194967

(51) Int. Cl.
*A61K 49/22* (2006.01)
*A61K 49/00* (2006.01)
*A61K 9/00* (2006.01)
*A61K 9/50* (2006.01)

(52) U.S. Cl.
CPC .......... *A61K 49/221* (2013.01); *A61K 9/0009* (2013.01); *A61K 9/5026* (2013.01); *A61K 49/0034* (2013.01); *A61K 49/0036* (2013.01); *A61K 49/0039* (2013.01); *A61K 49/0054* (2013.01); *A61K 49/0093* (2013.01); *A61K 49/223* (2013.01)

(58) Field of Classification Search
CPC ................ A61K 9/0009; A61K 9/5026; A61K 49/0034; A61K 49/0036; A61K 49/0039; A61K 49/0054; A61K 49/0093; A61K 49/221; A61K 49/223
See application file for complete search history.

(56) References Cited

U.S. PATENT DOCUMENTS

2011/0014297 A1  1/2011  Lee et al.

FOREIGN PATENT DOCUMENTS

| EP | 2474327 A1 | 7/2012 |
|---|---|---|
| WO | 2011053803 A2 | 5/2011 |
| WO | 2013053042 A1 | 4/2013 |

OTHER PUBLICATIONS

Briggs et al., Non-invasive Monitoring of Ultrasound-Stimulated Microbubble Radiation Enhancement Using Photoacoustic Imaging, Technology in Cancer Research and Treatment, 2014, pp. 435-444, vol. 13(5).
Fan et al., SPIO-conjugated, doxorubicin-loaded microbubbles for concurrent MRI and focused-ultrasound enhanced brain-tumor drug delivery, Biomaterials, 2013, pp. 3706-3715, vol. 34.
Fokong et al., Advanced Characterization and Refinement of Poly N-Butyl Cyanoacrylate Microbubbles for Ultrasound Imaging, Ultrasound in Med. & Biol., 2011, pp. 1622-1634, vol. 37(10).
Fokong et al., Image-guided, targeted and triggered drug delivery to tumors using polymer-based microbubbles, Journal of Controlled Release, 2012, pp. 1-7.
Hannah et al., Indocyanine Green-Loaded Photoacoustic Nanodroplets—Dual Contrast Nanoconstructs for Enhanced Photoacoustic and Ultrasound Imaging, ACS Nano., 2014, 250-259, vol. 8(1).
Huynh et al., Porphyrin Shell Microbubbles with Intrinsic Ultrasound and Photoacoustic Properties, Journal of American Chemical Society, 2012, pp. 16464-16467, vol. 134.
Jayapaul et al., FMN-coated fluorescent iron oxide nanoparticles for RCP-mediated targeting and labeling of metabolically active cancer and endothelial cells, Biomaterials, 2011, pp. 5863-5871, vol. 32.
Khalafalla et al., Preparation of Dilution-stable Aqueous Magnetic Fluids, IEEE Transactions on Magnetics, 1980, pp. 178-183, vol. 16(2).
Koczera et al., Fluorescently labeled microbubbles for facilitating translational molecular ultrasound studies, Drug Deilv. and Transl. Res., 2012, pp. 56-64, vol. 2.
Lammers et al., Theranostic USPIO-Loaded Microbubbles for Mediating and Monitoring Blood-Brain Barrier Permeation, Adv. Funct. Mater, 2014, pp. 1-8.
Laurent et al., Magnetic Iron Oxide Nanoparticles: Synthesis, Stabilization, Vectorization, Physicochemical Characterizations, and Biological Applications, Chem. Rev., 2008, pp. 2064-2110, vol. 108.
Wang et al., Photoacoustic/ultrasound dual-modality contrast agent and its application to thermotherapy, Journal of Biomedical Opitcs, 2012, pp. 1-9, vol. 7(4).
Wilson et al., Acoustic and Photoacoustic Molecular Imaging of Cancer, J. Nucl. Med., 2013, pp. 1851-1854, vol. 54(11).

*Primary Examiner* — Zohreh A Fay
(74) *Attorney, Agent, or Firm* — The Webb Law Firm

(57) ABSTRACT

The invention provides a multimodal ultrasound and photoacoustic contrast agent based on polymeric microparticles having a gas core and carrying at least one photoacoustic agent in its shell that stabilizes the gas core, for use in ultrasound and photoacoustic imaging. Such multimodal ultrasound and photoacoustic contrast agent is also suitable as a carrier of drugs and for use in photodynamic therapy, and for tissue imaging ex vivo.

14 Claims, 3 Drawing Sheets

MULTIMODAL ULTRASOUND AND PHOTOACOUSTIC CONTRAST AGENT BASED ON POLYMERIC MICROPARTICLES

CROSS-REFERENCE TO RELATED APPLICATIONS

This application is the United States national phase of International Application No. PCT/EP2015/077827 filed Nov. 26, 2015, and claims priority to European Patent Application No. 14194967.7 filed Nov. 26, 2014, the disclosures of which are hereby incorporated in their entirety by reference.

BACKGROUND OF THE INVENTION

Field of the Invention

The invention provides a multimodal ultrasound and photoacoustic contrast agent based on poly(n-butyl cyanoacrylate) microparticles having a gas core and carrying at least one photoacoustic agent in its poly(n-butyl cyanoacrylate) shell that stabilizes the gas core, for use in ultrasound and photoacoustic imaging. Such multimodal ultrasound and photoacoustic contrast agent is also suitable as a carrier of drugs and for use in photodynamic therapy, and for tissue imaging ex-vivo.

Description of Related Art

Photoacoustic imaging is a rapidly developing technology enabling a sensitive assessment of molecular and functional tissue characteristics, e.g. for superficial pathologies, in endoscopic applications and during surgical interventions. It complements ultrasound imaging, which has better penetration depth but lower spatial resolution for superficial lesions. Thus, multimodal contrast agents applicable in both modalities will be of benefit for many applications. So far porphyrin shell microbubbles (porphyrin-phospholipid conjugate based photonic microbubbles) with intrinsic ultrasound and photoacoustic properties are described in E. Huynh et al., JACS 134:16464-16467 (2012); Indocyanine Green-loaded photoacoustic nanodroplets for enhanced photoacoustic and ultrasound imaging are described in A. Hannah et al., ACS Nano (2013); acoustic and photoacoustic molecular imaging of cancer is described in K. E. Wilson et al., J. Nucl. Med. 54(11):1851-1854 (2013); non-invasive monitoring of ultrasound-stimulated microbubble radiation enhancement using photoacoustic imaging is described in K. Briggs et al., Technol. Cancer Treat. (2013); and photoacoustic/ultrasound dual modality contrast agents and its application to thermotherapy are described in Y. H. Wang et al., J. Biomed. Opt 14(7):045001 (2012).

Further, multi-functional biodegradable particles for selectable targeting, imaging and delivery of therapeutic agents with a core comprising a photoacoustic agent are known from WO2011/053803.

On the other hand, poly (n-butyl cyanoacrylate) (PCBA)-based hard-shell microbubbles, which are generally known for functional and molecular ultrasound imaging, can also be labeled with fluorophores and/or antibodies and be loaded with drugs (P. Koczera et al., Drug Deliv. and Transl. Res. 2:56-64 (2012) and S. Fokong et al., J. Controlled Release (2012), doi:10.1016/j.jconrel.2012.05.007). Poly (n-butyl cyanoacrylate) (PCBA)-based microbubbles that carry ultrasmall superparamagnetic iron oxide nanoparticles in their shell in their shell are known to be suitable for mediating and monitoring blood-brain barrier permeation (T. Lammers et al., Adv. Funct. Mater. (2014), Doi:10.1002/sdfm.201401199).

SUMMARY OF THE INVENTION

It has now been found that a multimodal contrast agent obtainable by the entrapment (encapsulation, adhesion and/or binding) of fluorophores (such as indocyanine green (ICG), india ink, methylene blue, melanin or porphyrins) and photoacoustic active species (such as gold nanoparticles and iron oxide nanoparticles) into the shell of poly n-butyl-cyanoacrylate microbubbles is particularly suitable for ultrasound and photoacoustic imaging, including, among others, skin cancer characterization, sentinel lymph node mapping, endometriosis detection, laparoscopic, endoscopic or surgical tumor localization but also characterization of arthritis, atherosclerosis and vascular inflammation, and image-guided drug delivery across the blood-brain barrier.

The invention thus provides (1) a multimodal ultrasound and photoacoustic contrast agent based on poly(n-butyl cyanoacrylate) (PBCA) microparticles (hereinafter shortly referred to as "microbubbles") having a gas core and carrying at least one photoacoustic agent in its PBCA shell that stabilizes the gas core, for use in ultrasound and photoacoustic imaging;

(2) a multimodal ultrasound and photoacoustic contrast agent as defined in (1) above for use as a carrier of drugs and for use in photodynamic therapy;

(3) the use of the multimodal ultrasound and photoacoustic contrast agent as defined in (1) above for tissue imaging ex vivo; and (4) a method for ultrasound and photoacoustic imaging in vivo and ex vivo comprising (a) applying the multimodal ultrasound and photoacoustic contrast agent defined in (1) above to the target tissue to be imaged, (b) photoacoustic visualization of the target tissue, and (c) evaluating the visualized target tissue.

DETAILED DESCRIPTION

Figure 1:
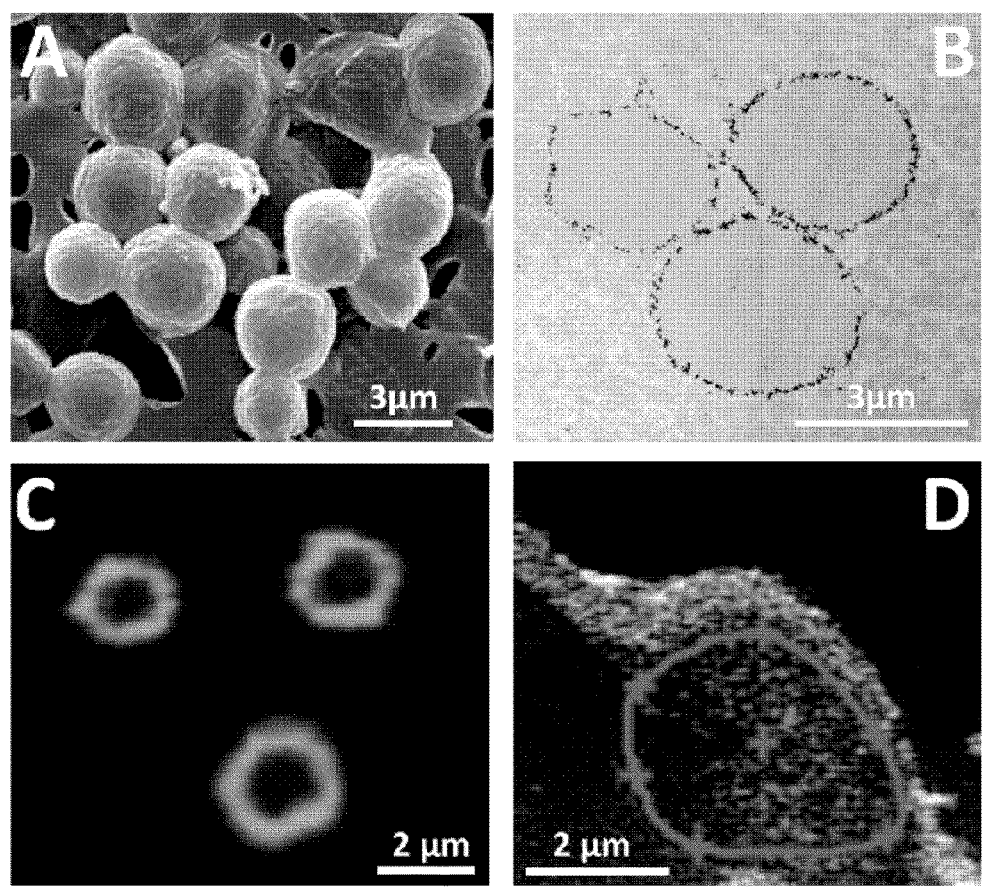
FIG. 1: Structure and ultrasound contrast enhancement of polymeric microbubbles.

In the multimodal ultrasound and photoacoustic contrast agent of aspect (1) said at least one photoacoustic agent can be a fluorophore is selected from indocyanine green (ICG), india ink, methylene blue, melanin or porphyrins, or a photoactive specie is selected from gold nanoparticles and iron-oxide nanoparticles or a combination thereof. Further, said at least one photoacoustic agent may be entrapped by, namely encapsulated by, adhered to or bound to, the polymeric microbubble.

The microbubbles suitable for multimodal ultrasound and photoacoustic contrast agent are obtainable by emulsion polymerization, wherein the photoacoustic agent is added before polymerization or to pre-formed microbubbles or is covalently attached to pre-formed and surface-modified microbubbles.

The polymer forming the shell of the microbubble is partially or completely composed of poly(n-butyl cyanoacrylate). Further constituents include polylactic acid, denaturated proteins, a sugar or a combination thereof. The microbubbles with a shell completely composed of poly(n-butyl cyanoacrylate) are preferred.

The shell generally has thickness of 10 to 100 nm.

The gas core of the microbubbles can be filled with air, oxygen, a perfluorocarbon and/or sulfohexafluoride.

According to the invention the contrast agent has an absorbance and emission in the microdosis range. It is particularly preferred that the contrast agent has a ratio of an absorbance for light having a wavelength of 895 nm to an absorbance for light having a wavelength of 780 nm is 0.1 or more. Also the size of the microbubble can be in the nano (>500 nm) to micro (<8 μm) range.

It is also preferred that the microbubbles further carry targeting moieties specifically binding to molecular markers in vivo, preferably said targeting moieties are antibodies (including polyclonal and monoclonal antibodies) and members of specific binding pairs (such as biotin-streptavidin). Alternatively, the surface of the microbubbles may be further covered with polyethylene glycol.

The multimodal ultrasound and photoacoustic contrast agent may be dispersed in a dispersion medium (such as sodium chloride, PBS, HBSS or any other physiological buffer) in which the microbubbles are dispersed, or they may be in the form of a lyophilized powder that can be re-suspended before use.

The multimodal ultrasound and photoacoustic contrast agent of aspect (1) of the invention is preferably for functional and/or molecular imaging of diseases, such as sentinel lymph node mapping, tumor detection including endometriosis, vascular characterization, including inflammation, angiogenesis and atherosclerosis, arthritis, and image-guided drug delivery across the blood-brain barrier. In can be applied in preclinical research, veterinary medicine or at human patients.

Such ultrasound and photoacoustic imaging preferably comprises
(a) applying the multimodal ultrasound and photoacoustic contrast agent to the target tissue to be imaged in vivo,
(b) photoacoustic visualization of the target tissue, and
(c) evaluating the visualized target tissue.

A destruction of the microbubbles may lead to release of photoacoustically active species and local enhancement of photoacoustic signals.

The invention will be furthermore explained in the following Examples depicted in FIGS. 1-5.

EXAMPLES

Materials: n-butyl cyanoacrylate (BCA) was obtained from Special Polymer Ltd, potassium ferrocyanide from AppliChem, and iron(III) chloride, iron(II)chloride tetrahydrate, FITC-dextran (70 kDa), Triton X-100 and Nuclear Fast Red solution from Sigma Aldrich. Ammonium hydroxide solution (NH3.$H_2O$, 25%) was obtained from Carl Roth GmbH.

Synthesis and Characterization of USPIO and USPIO-MB: Ultrasmall super-paramagnetic iron oxide (USPIO) nanoparticles were prepared using a standard co-precipitation method of ferrous and ferric salts (S. E. Khalafalla, G. W. Reimers, IEEE Trans. Magn. 16:178 (1980)). Briefly, $FeCl_3$ (16 mmol; 2.66 g) and $FeCl_2.4H_2O$ (8 mmol; 1.63 g) were dissolved in deionized water. An aqueous ammonia solution (25%, NH 3.$H_2O$, 4 ml) was then added drop-wise, followed by 10 min of vigorous stirring at 1500 rpm. After stirring, a permanent magnet was used to isolate the precipitated iron oxide nanoparticles, which were washed three times by re-dispersion in deionized water. The purified USPIO were physicochemically analyzed and subsequently stored in 40 ml of diluted HCl (0.02 M) S. Laurent et al, Chem. Rev. 108:2064 (2008)).

The properties of the USPIO nanoparticles were: core size (as determined by transmission electron microscopy) =5.5±1.1 nm; hydrodynamic diameter and polydispersity (as determined by dynamic light scattering, in HEPES buffer, pH 7) 252±66 nm and 0.35, respectively; zeta potential (as determined using nanosizer, at pH 7)=18.9±2.5; molar ratio $Fe^{2+}:Fe^{3+}$=1:2; and crystallinity (as determined using X-ray diffraction)=typical highly crystalline magnetite diffraction pattern, in line with JCPDS No. 19.0629. The longitudinal ($r_1$) and transversal ($r_2$) relaxivity of the nanoparticles could not be determined, because of aggregation in water at pH 7, which results in susceptibility artifacts (J. Jayapaul et al., Biomaterials 32:5863 (2011)). MB with and without USPIO nanoparticles were synthesizedas previously described (S. Fokong et al, Ultrasound Med. Biol. 2011, 37:1622 (2011)). USPIO-MB were synthesized by adding 3 ml of n-butyl cyanoacrylate (BCA) monomer to an aqueous solution containing 1% (w/v) Triton X-100 and 225 mg of pre-synthesized USPIO nanoparticles; regular MB were prepared similarly, but without USPIO nanoparticles in solution (C. H. Fan et al., Biomaterials, 34: 3706 (20013)). The mixture was stirred for 60 min at 10 000 using an Ultra-turrax mixer (IKA-Werke), giving rise to PBCA-MB containing USPIO in their shell. Subsequently, USPIO-MB were purified and size-isolated by two sequential rounds of centrifugation at 500 rpm for 10 min. After each centrifugation step, the MB were re-dispersed in an aqueous solution containing 0.02% (w/v) triton X-100. The mean diameter, size distribution and concentration of the USPIO-MB were analyzed using a Multisizer 3 (Beckman Coulter). The average shell thickness (determined on the basis of 50 individual MB), shape and surface morphology of the MB were visualized using cryo-scanning electron microscopy (FESEM, Hitachi-S4800). The encapsulation of USPIO into the MB shell was visualized using transmission electron microscopy (TEM; Philips EM400T). The iron concentration in USPIO-MB was analyzed using inductively coupled plasma mass spectrometry (ICP-MS; Elan-DRCII; Perkin Elmer). This was done in triplicate, in a solution containing $10^8$ MB.

FIG. 1: Structure and ultrasound contrast enhancement of polymeric microbubbles. A depicts the surface morphology of the particles by scanning electron microscopy. The encapsulation of e.g. iron-oxide nanoparticles in the shell is shown in B, while the ability to load dye molecules (e.g. coumarin-6) into the shell is shown in C. Acoustic contrast enhancement of the particles e.g. in a subcutaneous tumor (delineated region) is depicted in D.

Figure 2:
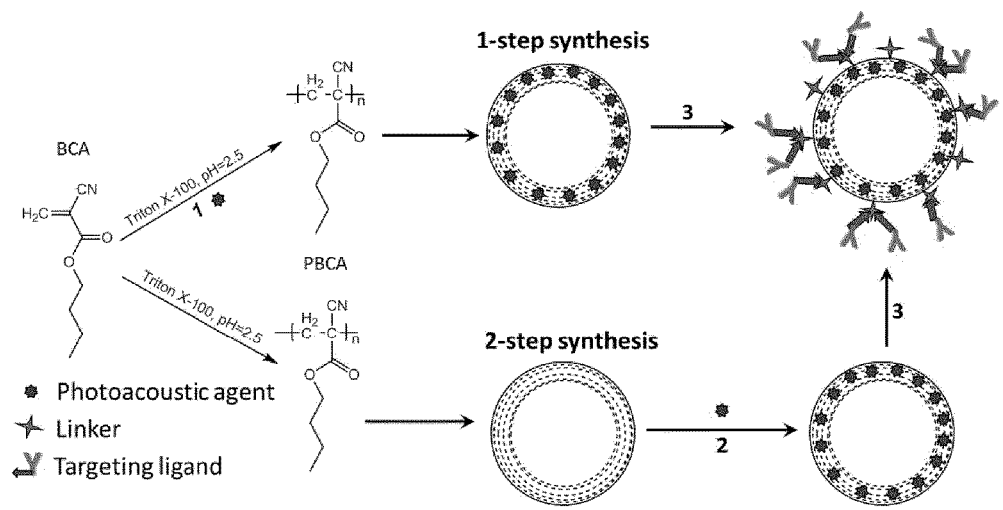
FIG. 2: Schematic of the synthesis of microbubbles for ultrasound and photoacoustic (PA) imaging.

FIG. 2: Schematic of the synthesis of microbubbles for ultrasound and photoacoustic (PA) imaging. In this example, the synthesis of poly n-butylcyanoacrylate (PBCA) microbubbles by rapid stirring of an aqueous solution containing 1% (v/v) triton x-100 and the monomer (n-butylcyanoacrylate) at pH 2.5 is shown. The incorporation of photoacoustic agents in/on the shell of the microbubbles can be achieved by adding the agents during (1-step method) or after (2-step method) synthesis of the microbubbles. A purification of the PA-agent carrying microbubbles can be achieved by several rounds of flotation or centrifugation. For both 1- and 2-step synthesized microbubbles, the attachment of targeting ligands to the microbubble surface can be achieved by a subsequent hydrolysis of the butyl ester side chains to create carboxylate groups to which targeting ligands can be attached for example by amine bonding.

Figure 3:
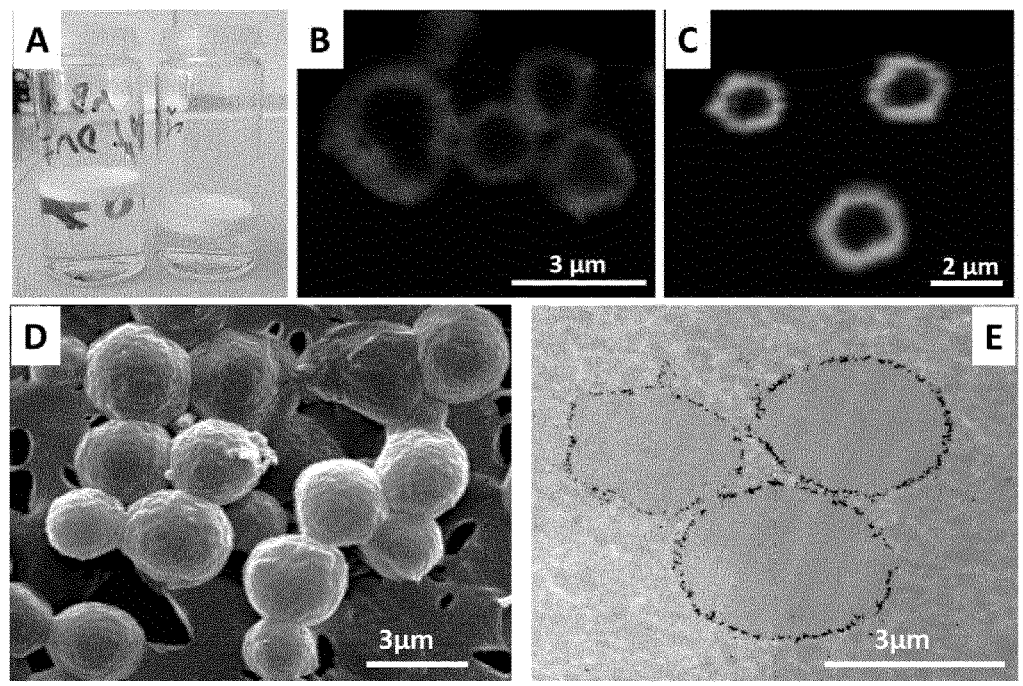
FIG. 3: Effect of the loading of microbubbles.

FIG. 3: After synthesis and purification, the incorporation of the PA-agents in/on to the MB shell can be visually confirmed microbubble color change. A shows an image of regular microbubbles and indo-cyanine green (ICG) loaded microbubbles. The successful loading of ICG led to a greenish color of the floating MB pellet, which can be differentiated from the white color of regular microbubbles. B-C demonstrates further validation of the loading of PA-agents into the PBCA-microbubbles. In these examples, the validation of PA-agent loading is done by fluorescence microscopy. B represents a fluorescence confocal microscopic image of temoporfin loaded microbubbles while C shows a two-photon laser scanning microscope image of coumarin-6 loaded microbubble. For nanoparticle PA-agents that are non-fluorescent, the incorporation into the MB shell can be studied by electron microscopy. D shows a scanning electron microscope image of iron-oxide nanoparticles loaded PBCA-microbubbles, revealing a rough shell surface. By transmission electron microscopy of the same iron-oxide nanoparticle loaded microbubbles (E), the arrangement of the iron-oxide nanoparticles in the shell of the microbubbles can be clearly visualized.

Figure 4:
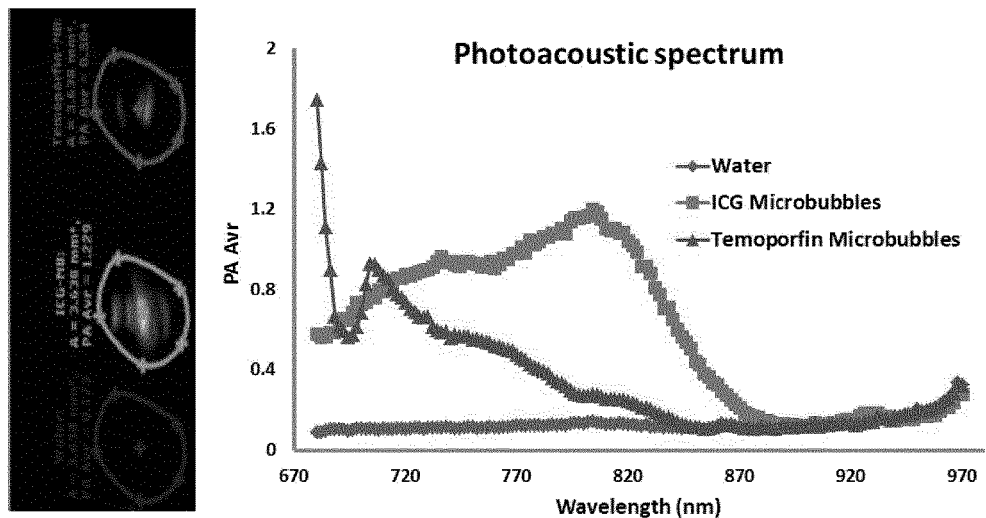
FIG. 4: Photoacoustic characterization of PBCA-microbubbles loaded with temoporfin or ICG.

FIG. 4: Photoacoustic characterization of PBCA-microbubbles loaded with temoporfin or ICG. The microbubbles were injected into a polyethylene tube with an inner diameter of 0.3 mm and imaged using preclinical combine ultrasound and photoacoustic device (Vevo 2100+ LAZR: Visualsonics, Amsterdam). The graph shows the photoacoustic spectrum of the different PA-agent carrying microbubbles compared to water (regular PBCA-microbubbles are not photoacoustically active and therefore have a spectrum like water). The signal enhancement compared to water shown in the graph is therefore as a result of agents entrapped in the microbubbles shell, thereby highlighting the suitability of these constructs for photoacoustic imaging.

Figure 5:
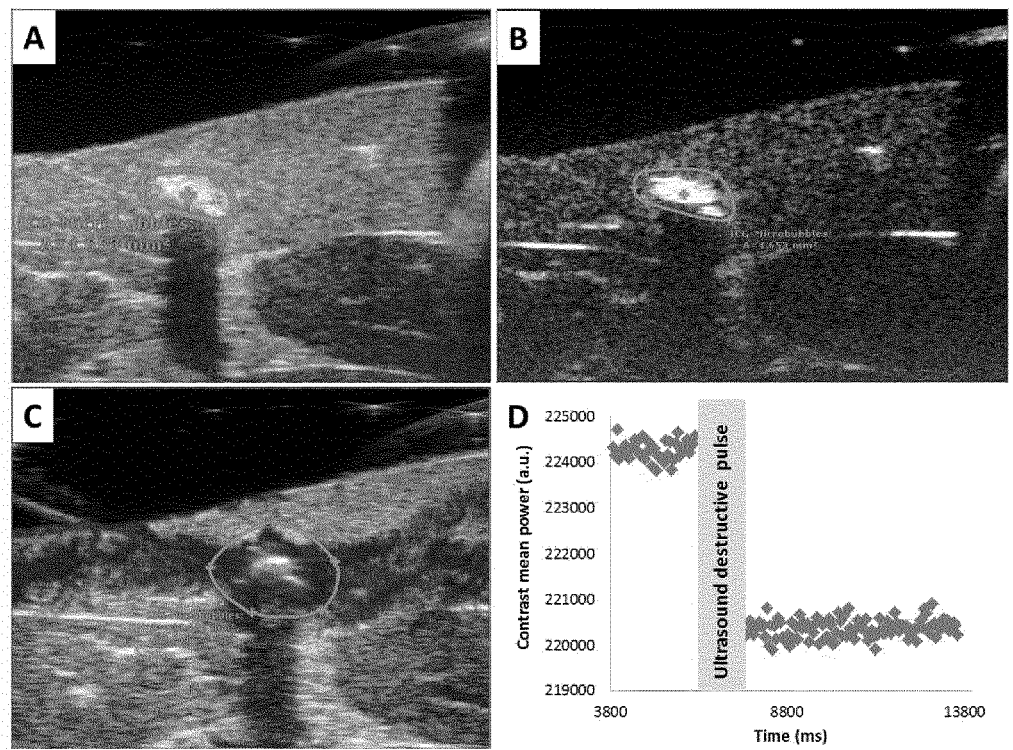
FIG. 5: Ex vivo hybrid ultrasound and photoacoustic imaging of ICG-loaded PBCA-microbubbles injected into a piece of chicken breast.

FIG. 5: Ex-vivo hybrid ultrasound and photoacoustic imaging of ICG-loaded PBCA-microbubbles injected into a piece of chicken breast. The ultrasound signal enhancement by the microbubbles in both B-mode and contrast-mode imaging is shown in A and B respectively (ROI shows the injected microbubbles. Also notice the shadow casted beneath the microbubbles due to total reflection of the ultrasound waves). C shows a hybrid ultrasound/photoacoustic image of the same region as in A and B, indicating a strong photoacoustic signal from the microbubbles. Application of a high mechanical index destructive ultrasound pulse led to microbubble destruction (as expected) and therefore a reduction in ultrasound signal intensity in the region (D). In a nutshell, this ex-vivo study demonstrates the ability to detect such PA-agent carrying microbubble by both ultrasound and photoacoustic imaging.

The invention claimed is:

1. A multimodal ultrasound and photoacoustic contrast agent, comprising for use in ultrasound and photoacoustic imaging poly(n-butyl cyanoacrylate) (PBCA) microparticles (microbubbles) having a gas core and carrying at least one photoacoustic agent in its PBCA shell that stabilizes the gas core.

2. The multimodal ultrasound and photoacoustic contrast agent for use in ultrasound and photoacoustic imaging of claim 1, wherein
   (i) said at least one photoacoustic agent is a fluorophore is selected from indocyanine green (ICG), india ink, methylene blue, melanin, polydopamine or porphyrins, or a photoactive species is selected from gold nanoparticles and iron-oxide nanoparticles or a combination thereof; and/or
   (ii) said at least one photoacoustic agent is entrapped by the PBCA shell of the microbubble.

3. The multimodal ultrasound and photoacoustic contrast agent for use in ultrasound and photoacoustic imaging of claim 1, wherein
   (i) the microbubbles are obtainable by emulsion polymerization, wherein the photoacoustic agent is added before polymerization or to pre-formed microbubbles or is covalent attached to pre-formed and surface modified microbubbles; and/or
   (ii) the polymer forming the microbubble is completely composed of poly(n-butyl cyanoacrylate); and/or
   (iii) the shell has thickness of 10 to 100 nm.

4. The multimodal ultrasound and photoacoustic contrast agent for use in ultrasound and photoacoustic imaging of claim 1, wherein the gas core of the microbubbles is composed of air, oxygen, sulfohexafluoride, and/or a perfluorocarbon.

5. The multimodal ultrasound and photoacoustic contrast agent for use in ultrasound and photoacoustic imaging of claim 1, wherein
   (i) the contrast agent has an absorbance and emission in the microdosis range; and/or
   (ii) the size of the microbubble is in the nano (>500 nm) to micro (<8μm) range.

6. The multimodal ultrasound and photoacoustic contrast agent for use in ultrasound and photoacoustic imaging of claim 1, wherein the microbubble further carries targeting moieties specifically binding to molecular markers in vivo.

7. The multimodal ultrasound and photoacoustic contrast agent for use in ultrasound and photoacoustic imaging of claim 1, wherein the surface of the microbubble is further covered with polyethylene glycol.

8. The multimodal ultrasound and photoacoustic contrast agent for use in ultrasound and photoacoustic imaging of claim 1, wherein the contrast agent is dispersed in a dispersion medium in which the microbubbles are dispersed, or is in the form of a lyophilized powder can be re-suspended before use.

9. The multimodal ultrasound and photoacoustic contrast agent for use in ultrasound and photoacoustic imaging of claim 1, which is for functional and/or molecular imaging of diseases, such as sentinel lymph node mapping, tumor detection including endometriosis, vascular characterization, including inflammation, angiogenesis and atherosclerosis, arthritis, and image-guided drug delivery across the blood-brain barrier.

10. The multimodal ultrasound and photoacoustic contrast agent for use in ultrasound and photoacoustic imaging of claim 1, wherein the ultrasound and photoacoustic imaging comprises
    (a) applying the multimodal ultrasound and photoacoustic contrast agent to the target tissue to be imaged in vivo,
    (b) photoacoustic visualization of the target tissue, and
    (c) evaluating the visualized target tissue.

11. The multimodal ultrasound and photoacoustic contrast agent for use in ultrasound and photoacoustic imaging of claim 1, wherein a destruction of the microbubbles leads to release of photoacoustic active species and local enhancement of photoacoustic signals.

12. The multimodal ultrasound and photoacoustic contrast agent as defined in claim 1 for use as a carrier of drugs and for use in photodynamic therapy.

13. The multimodal ultrasound and photoacoustic contrast agent for use in ultrasound and photoacoustic imaging of claim 5, wherein the contrast agent has a ratio of an absorbance for light having a wavelength of 895 nm to an absorbance for light having a wavelength of 780 nm is 0.1 or more.

14. The multimodal ultrasound and photoacoustic contrast agent for use in ultrasound and photoacoustic imaging of claim 6, wherein said targeting moieties are antibodies and members of specific binding pairs.

* * * * *